Figure 1:
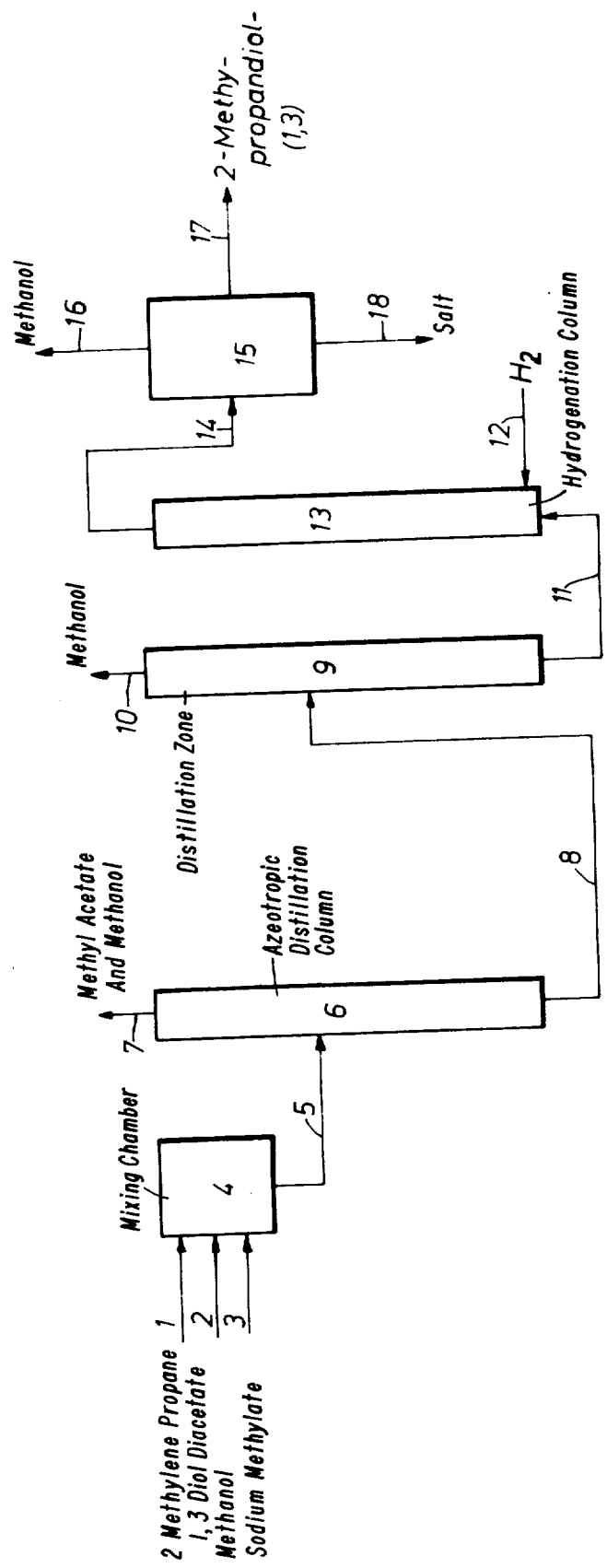

United States Patent [19]

Vogel et al.

[11] 4,036,895
[45] July 19, 1977

[54] PROCESS FOR PREPARING 2-METHYLPROPANE-1,3-DIOL

[75] Inventors: Axel Vogel, Cologne; Wolfgang Biedermann, Krefeld-Bockum; Kurt Halcour; Norbert Schenk, both of Leverkusen; Wulf Schwerdtel, Leverkusen-Steinbuechel, all of Germany

[73] Assignee: Bayer Aktiengesellschaft, Leverkusen, Germany

[21] Appl. No.: 507,173

[22] Filed: Sept. 18, 1974

[30] Foreign Application Priority Data

Sept. 26, 1973 Germany .................... 2348353

[51] Int. Cl.$^2$ .................................. C07C 29/00
[52] U.S. Cl. ........................ 260/635 R; 260/637 R
[58] Field of Search .................. 260/635 R, 642 D

[56] References Cited

FOREIGN PATENT DOCUMENTS

| 2,054,987 | 5/1972 | Germany | 260/635 R |
| 1,066,566 | 10/1959 | Germany | 260/635 R |
| 652,329 | 4/1951 | United Kingdom | 260/635 R |

OTHER PUBLICATIONS

Brewster, "J. Am. Chem. Soc.", vol. 73 (1951), pp. 366-370.
Lang, "Handbook of Chemistry", 10th ed. (1961) pp. 572-573, 710-711.

Primary Examiner—Joseph E. Evans
Attorney, Agent, or Firm—Burgess, Dinklage & Sprung

[57] ABSTRACT

2-Methylpropane-1,3-diol is prepared by reacting 2-methylenepropane-1,3-diol diacetate with a monohydric, lower aliphatic alcohol in the presence of a base. Thereafter the resulting 2-methylenepropane-1,3 diol is catalytically hydrogenated to form 2-methylpropane-1,3-diol.

9 Claims, 2 Drawing Figures

PROCESS FOR PREPARING 2-METHYLPROPANE-1,3-DIOL

BACKGROUND

The invention relates to a particularly advantageous process for preparing 2-methylpropane-1,3-diol from 2-methylenepropane-1,3-diol diacetate.

SUMMARY

We have found that 2-methylpropane-1,3-diol can be obtained from 2-methylenepropane-1,3-diol diacetate by reacting 2-methylenepropane-1,3-diol diacetate with at least the stoichiometrically required quantity of a monovalent lower aliphatic alcohol in the presence of bases, and catalytically hydrogenating the resulting 2-methylenepropane-1,3-diol without first isolating it.

Lower aliphatic alcohols are preferably alkanols containing from 1 to 4 carbon atoms, such as methanol, ethanol, propanol- 1, propanol- 2, butanol- 1, butanol- 2 or isobutanol. Methanol is preferably used. For the reaction of the known compound 2-methylenepropane-1,3-diol diacetate, it is necessary to use at least 2 mols of monohydric alcohol per mol of 2-methylenepropane-1,3-diol diacetate in accordance with the stoichiometric requirements.

If the resulting alkyl acetate is removed from the reaction mixture by distillation, and if this alkyl acetate forms an azeotropic mixture with the monohydric alcohol used, the quantity of alcohol required in the reaction mixture is, of course, more than the stoichiometric equivalent. The total requirement therefore depends on the nature of the alcohol used. The alcohol is generally used in excess of the stoichiometric quantity. To avoid unnecessarily high dilutions, however, which would increase the time required for distillation, an excess of 0.1 to 40 mol, preferably 0.14 to 20 mol per mol of 2-methylenepropane-1,3-diol diacetate may suitably be used.

The reaction of 2-methylenepropane-1,3-diol diacetate with the lower alcohol is carried out in the presence of a base. It is advantageous to use strong bases for this purpose, such as alkali metal alcoholates, preferably the alkali metal alcoholates of the alcohol used for example, sodium methylate or sodium ethylate, or alkali metal hydroxides (preferably sodium hydroxide or potassium hydroxide) or alkaline earth metal hydroxides, for example calcium hydroxide. Alkali metal carbonates such as sodium carbonate or potassium carbonate may, of course, also be used, or other alkalis of comparable strength. Mixtures of the above-mentioned bases may, of course, be used. Ion exchangers which are basic in reaction may also be used.

The bases are generally used in quantities of from 0.01 to 5 parts by weight, preferably from 0.1 to 1 part by weight, for every 100 parts by weight of 2-methylenepropane-1,3-diol diacetate.

The usual hydrogenation catalysts used for hydrogenating olefinic double bonds may be used, for example Raney nickel, Raney nickel-iron, finely divided nickel on suitable carriers, e.g. on kieselguhr, or ion exchangers, various noble metals, particularly platinum, ruthenium, rhodium or iridium. These catalysts may be used alone or in combination, optionally together with promoters. Suitable promoters are e.g. rhenium, cadmium, iron, chromium, copper, silver, gold, vanadium, molybdenum and tungsten. The promoters are generally used in quantities of up to 10 parts by weight, preferably up to 4 parts by weight, for each part by weight of catalyst metal. The catalysts may be used in bulk, particularly the skeleton catalysts, or finely divided on carriers. Suitable carriers include active charcoals, aluminium oxides, silicic acid, pumice stone, spinels such as lithium aluminium spinel or the like. In cases where carriers are used, the finished catalyst advantageously contains from 0.5 to 50 g of metal per liter of catalyst.

The preferred catalysts are Raney nickel or Raney nickel-iron, or rhodium or ruthenium, optionally in combination with rhenium. The catalysts may be used either in a finely divided form, e.g. as a powder, or in particle form, e.g. as pellets or balls or crushed.

The reaction of 2-methylenepropane-1,3-diol diacetate with the monohydric alcohol is generally carried out at a temperature between 0° and 200° C, preferably at the reflux temperature of the reaction mixture. It is preferably carried out at normal to slightly elevated pressure (5 bar), although reduced or more elevated pressure may also be employed.

Hydrogenation can be carried out with high yields at temperatures between $-20°$ C and 180° C. It is preferably carried out at a temperature of from 0° to 150° C, in particular from 20° to 100° C.

A hydrogen pressure of about 1 bar is generally sufficient for hydrogenation although it is in most cases advantageous, e.g. to obtain short hydrogenation times, to employ higher hydrogen pressures (e.g. up to 300 bar, preferably up to 200 bar). The upper pressure limit is set purely by technical circumstances. Operation at elevated hydrogen pressures is also advisable because the selectivity and hence also the yield of 2-methylpropane-1,3-diol generally increase with increasing hydrogen pressure. It may also be advisable, in order to prevent initial overheating due to inefficient cooling of the hydrogenation autoclave, to start hydrogenation at a low hydrogen pressure and then increase the pressure either stepwise or continuously in the course of the reaction.

A reaction mixture generally containing 0.1 to 30 mol, preferably 0.14 to 10 mol of excess alcohol per mol of 2-methylenepropane-1,3-diol diacetate, may be used for hydrogenation. The desired concentration is normally obtained by measuring out the correct quantity of alcohol before the reaction with 2-methylenepropane-1,3-diol diacetate, or by removing excess alcohol after removal of the alkyl acetate formed in the reaction, for example by distillation. The quantity of alcohol required for hydrogenation may, if desired, be added to the reaction mixture after removal of the alkyl acetate. Dilution may, of course, be carried out with other organic solvents which are inert under the reaction conditions, instead of with the monohydric alcohol. For example, aliphatic or alicyclic ethers such as diethylether, diisopropylether, dibutylether, ethylene glycol dimethylether, tetrahydrofuran or 1,4-dioxane may be used for this purpose. The solvents are also used in the quantities mentioned above. The solvents may, of course, also be used in admixture with the lower aliphatic alcohol.

The reaction mixture used for hydrogenation preferably contains from 5 to 80% by weight of the lower aliphatic alcohol.

It is generally advisable to remove practically all the alkyl acetate from the reaction mixture before hydrogenation is carried out.

The reaction mixture may, of course, be purified before it is used for hydrogenation, e.g., tarry by-products can be substantially removed by treatment with active charcoal, or the bases may be partly or completely neutralised. The advantage of the process according to the invention, however, is that the crude reaction mixture can be used directly for hydrogenation.

The process according to the invention may be carried out discontinuously in simple apparatus. An ordinary reaction vessel is quite adequate for the reaction of 2-methylenepropane-1,3-diol diacetate with the lower monohydric alcohol. This reaction is suitably carried out in a distillation apparatus with an attached distillation column. 2-Methylenepropane-1,3-diol diacetate and the alcohol are in that case introduced into the sump of the column together with the added bases and heated, and the alkyl acetate formed is continuously removed from the head of the column, optionally as an azeotropic mixture. In another method of carrying out the process, only part of the reactants is introduced into the sump, and the remaining components are then added individually or together in the course of the reaction, either continuously or batchwise. After completion of the reaction, excess alcohol may be distilled off until the sump content has been concentrated to the desired extent, or alternatively the distillation sump is made up to the required dilution with monohydric alcohol or with some other diluent, for example dioxane, and then introduced into a hydrogenation apparatus, for example a hydrogenation autoclave. After the addition of hydrogenation catalyst (generally in quantities of from 0.1 to 50 parts by weight, preferably from 1 to 25 parts by weight; for every 100 parts by weight of 2-methylene propane-1,3-diol diacetate put into the process) and, if necessary, adjustment to the required hydrogenation temperature, hydrogen gas is forced in under pressure while the reactants are vigorously mixed, until the reaction mixture is saturated with hydrogen. When hydrogenation has been completed, the catalyst is removed by known methods, for example by filtration, centrifuging or decanting, and the low boiling components, e.g. the residual alcohol such as methanol, are then distilled off, and finally 2-methylpropane-1,3-diol is distilled off the latter preferably at reduced pressure.

A preferred embodiment of the process according to the invention is carried out continuously in suitable apparatus, e.g. tube reactors, circulating plants, tank cascades or columns. FIG. 1 shows an example of the apparatus which may be used for the process according to the invention. 2-Methylene-propane-1,3-diol diacetate, methanol and sodium methylate introduced through pipes 1, 2 and 3 are mixed in the mixing chamber 4 and fed into column 6 through pipe 5. Methyl acetate distils off as an azeotropic mixture with methanol and is removed from the head of the column through pipe 7. The sump product is conducted through pipe 8 into the concentrating column 9 in which methanol is distilled off, if necessary, and removed at the head of the column through pipe 10. The sump product obtained in this way is passed through pipe 11 into the hydrogenation column 13 which is supplied with hydrogen from pipe 12. The hydrogenation column can be operated in the trickling phase or sump phase on a solid bed catalyst, or in the sump phase on a fluidised catalyst. The hydrogenation product is finally led through pipe 14 into a distillation apparatus 15 in which the low boiling constituents, mainly the remaining methanol as well as 2-methyl propane-1,3-diol are fractionated from the salt sump and separated. Methanol 2-methylpropane-1,3-diol and the salt sump are removed through their respective pipes 16, 17 and 18. Suitable distillation apparatus (15) are known per se.

Figure 2:
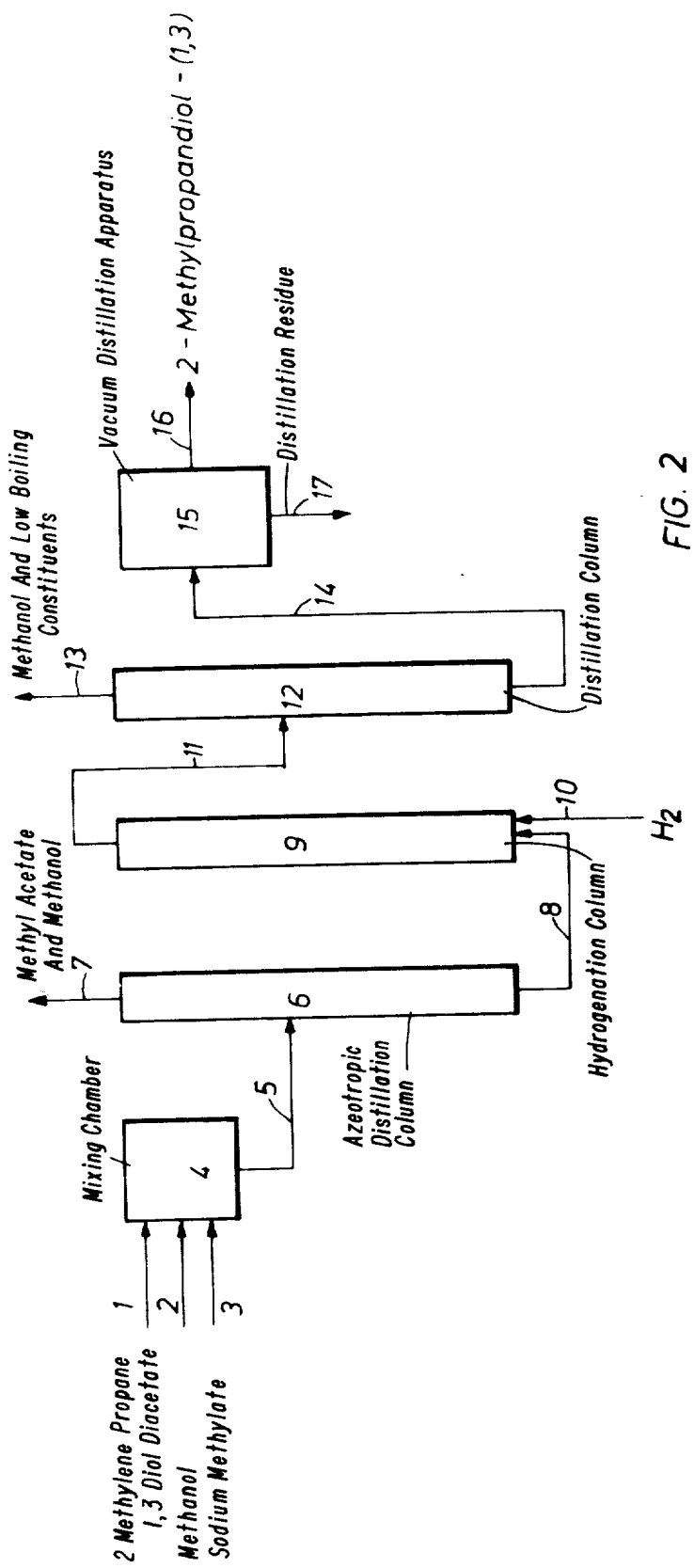

Another advantageous embodiment is shown by way of example in FIG. 2. The mixing chamber 4 is supplied with 2-methylenepropane-1,3-diol diacetate from pipe 1, methanol from pipe 2 and sodium methylate from pipe 3. The mixed components are then discharged through pipe 5 into the reaction column which is adjusted to the reflux temperature, and an azeotropic mixture of methyl acetate and methanol is drawn off at the head of the column through pipe 7. The sump product is discharged from the foot of the column 6 and passed through pipe 8 into the bottom of the hydrogenation column 9 which is supplied with hydrogen from pipe 10. The hydrogenation column may be operated in the trickling or sump phase on a solid bed catalyst, or in the sump phase on a fluidised bed catalyst. The hydrogenated product is transferred through pipe 11 into column 12, from which the low boiling constituents are removed at the top through pipe 13 while the hydrogenation product is discharged from the column through pipe 14 into a vacuum-operated distillation apparatus 15 in which 2-methylpropane-1,3-diol is distilled off and removed through pipe 16, while the distillation residue is discharged through pipe 17.

Instead of using reaction columns, the process could, of course, be carried out in other continuously operating apparatus such as tube reactors, circulation plants, tank cascades or autoclave cascades. Moreover, the process may be carried out as a combination of a discontinuous reaction with the lower alcohol and continuous hydrogenation, or conversely as a combination of a continuous reaction with the lower alcohol and discontinuous hydrogenation. In either case the products may be worked up continuously or discontinuously. It is preferred, however, to carry out the process continuously throughout.

The process according to the invention for the first time enables 2-methylpropane-1,3-diol to be produced on a technical scale. The starting material, 2-methylenepropane-1,3-diol diacetate, is already known and can easily be obtained, e.g. by the process according to DAS No. 1,909,964. A particular advantage of the process according to the invention is that no intermediate isolation of 2-methylenepropane-1,3-diol is necessary and even impure, crude 2-methylenepropane-(1,3)-diol, may be used for the catalytic hydrogenation.

These advantages of the process according to the invention are particularly surprising in view of the fact that simple solid-bed hydrogenation catalysts are found when tested over long periods to be particularly sensitive to impurities of various kinds. In the process according to the invention, however, the impurities coming from the preparation of 2-methylenepropane-1,3-diol diacetate as well as the by-product formed in the reaction, such as alkali metal alcoholates, alkali metal acetates and particularly the tar-like by-products, have no deleterious effect on the activity of the hydrogenation catalysts.

2-Methylpropane-1,3-diol, which can now be obtained satisfactorily and with high yields by the process according to the invention, is a primary aliphatic diol which is a valuable intermediate product, for example for the production of polyesters (J. prakt. Chem. N.F. Vol. 155, page 134 (1940); J. Polymer Sci., Vol. XVIII, pages 215-226 (1955)). In particular, in the production of polyhydroxypolyesters with OH numbers in the range of from 30 to 500 by the polycondensation of polyhydric alcohols with polybasic carboxylic acids, the velocity of esterification can be increased by using 2-methylpropane-1,3-diol as polyvalant alcohol, either alone or mixed with a maximum of 90 mols percent, based on the total quantity of alcoholic component, of other polyols. 2-Methylpropane-1,3-diol may be used also for the production of polyurethanes (see J. Amer. Soc. 73, page 368 (1951)).

The following Examples illustrate the invention.

EXAMPLE 1

A mixture of 2000 g of commercial 2-methylenepropane-1,3-diol diacetate of the following composition (analytical values):

- 94.9% by weight of 2-methylenepropane-1,3-diol diacetate,
- 1.5% by weight of acetic acid,
- 1.7% by weight of water,
- 0.2% by weight of methallylacetate,
- 0.5% by weight of acetoxyacetone,
- 0.4% by weight of 2-methylenepropane-1,3-diol acetate, and
- 0.8% by weight of unknown higher boiling substances, 4000 g of methanol and 80 g of sodium hydroxide are slowly heated under reflux in a 10 l three-necked flask equipped with stirrer, internal thermometer and fractionating attachment consisting of a 30 cm packed column and a dephlegmator at the head of the column. 2200 ml of an azeotropic mixture of methyl acetate and methanol boiling at 54° C are continuously removed from the head of the column and the temperature at the head of the column is then allowed to rise to the boiling point of pure methanol. When a total of 3000 ml of distillate has been removed, the blackish brown distillation sump product is introduced into a hydrogenation autoclave, about 30 g of Raney nickel moistened with methanol are added and the substance is hydrogenated at 20° C with cooling under a steady stream of hydrogen at 10 excess atmospheres until saturation is reached. After removal of the Raney nickel by filtration, the low boiling components are distilled off at normal pressure over a 30 cm packed column. The residue is then distilled off at 12 Torr. 905 g of colourless 2-methylpropane-1,3-diol are obtained, corresponding to 91% of the theoretical quantity; boiling point 110°–112° C/12 Torr; $n_D^{20}$ 1.4445.

EXAMPLE 2

2000 g of commercial 2-methylenepropane-1,3-diol diacetate having the following composition (analytical values):

- 96.3% by weight of 2-methylenepropane-1,3-diol diacetate,
- 0.5% by weight of acetic acid,
- 0.3% by weight of water,
- 0.1% by weight of methallylacetate,
- 0.2% by weight of acetoxyacetone,
- 0.5% by weight of 2-methylenepropane-1,3-diol acetate,
- 1.1% by weight of unknown higher boiling substances, and
- 1.0% by weight of polymer are heated to boiling together with 4000 g of methanol and 40 g of sodium methylate. About 2200 ml of an azeotropic mixture of methyl acetate and methanol are first removed from the head of the column, followed by a mixture with a higher methanol content. Distillation is continued until the sump has been concentrated to a volume of about 1500 ml. The sump product is then diluted with 2500 ml of 1,4-dioxane, 20 g of Raney nickel-iron (80:20) are then added and gaseous hydrogen are introduced under pressure in a hydrogenation autoclave at 20° C with cooling. The hydrogen pressure is adjusted to the rate of cooling. It is therefore initially 2 excess atmospheres and is subsequently raised to 20 excess atmospheres. When hydrogenation is completed, the catalyst is filtered off and the filtrate is fractioned by distillation, first at normal pressure and then at 12 Torr. 867 g (86% of the theoretical quantity) of 2-methylpropane-1,3-diol are obtained; boiling point 110°–112° C/12 Torr; $n_D^{20} = 1.4444$.

EXAMPLE 3

1000 g of distilled 2-methylenepropane-1,3-diol diacetate (99.8%), 800 g of methanol and 7.5 g of sodium methylate are heated and the resulting methyl acetate is continuously distilled off at the head of a column as an azeotropic mixture with methanol. Finally, methanol is distilled off until the sump has been concentrated to 600 g. The sump product is then introduced into a hydrogenation autoclave, 100 g of Raney nickel moistened with methanol are added and hydrogen is forced in at a pressure of 15 excess atmospheres at 130° C. When the uptake of hydrogen is completed, the liquid hydrogenation product contains 70% by weight of 2-methylpropane-1,3-diol, which is isolated by distillation. 416 g (80% of the theoretical quantity) of 2-methylpropane-1,3-diol are obtained.

EXAMPLE 4

1000 g of distilled 2-methylenepropane-1,3-diol diacetate (99.8%), 3000 g of methanol and 10 g of sodium methylate are heated together and the resulting methyl acetate is continuously distilled off the head of the column as an azeotropic mixture with methanol. Finally, methanol is distilled off until the sump has been concentrated to 2000 g. The sump product is then introduced into a hydrogenation autoclave, 250 ml of hydrogenation catalyst consisting of 1.0% by weight of ruthenium and 0.5% by weight of rhenium on spherical particles of lithium aluminium spinel are added, and hydrogen is forced in at room temperature, initially at a pressure of 16 excess atmospheres. The reaction temperature rises to 70° C and is maintained at that level by continuous increase of the hydrogen pressure to 50 excess atmospheres. After saturation with hydrogen, the hydrogenation product contains 21.2% by weight of 2-methylpropane-1,3-diol, which corresponds to a yield of 83% of the theoretical quantity.

EXAMPLE 5

1000 g of distilled 2-methylenepropane-1,3-diol diacetate (99.2%), 3000 g of methanol and 10 g of sodium methylate are heated together and the resulting methyl acetate is distilled off from a column as an azeotropic mixture with methanol. Finally, methanol is distilled off until the sump has been concentrated to 2000 g. The sump product is introduced into a hydrogenation autoclave, 250 ml of hydrogenation catalyst consisting of 1.0% ruthenium on spherical particles of aluminium oxide carrier are added, and hydrogen is forced in under a pressure of 16 excess atmospheres at room temperature. The reaction temperature is left to rise to 70° C. After saturation, the hydrogenation product contains 21.6% by weight of 2-methylpropane-1,3-diol, which corresponds to a yield of 84% of the theoretical quantity.

EXAMPLE 6

660 g of distilled 2-methylenepropane-1,3-diol diacetate (99.2%), 1200 g of methanol and 10 g of sodium methylate are heated together and the resulting methyl acetate is continuously distilled off from a column as an azeotropic mixture with methanol. Finally methanol is distilled off until the sump has been concentrated to 1040g. The sump product is introduced into a hydrogenation autoclave, 100 ml of hydrogenation catalyst consisting of 0.5% by weight of rhodium on spheres of lithium aluminium spinel are added, and hydrogenation is carried out at a hydrogen pressure of 16 excess atmospheres at 30° C with cooling. The yield of 2-methylpropane-1,3-diol is 83% of the theoretical quantity.

EXAMPLE 7

This Example is based on a continuously operating plant as shown in FIG. 1. 2.400 kg per hour of 2-methylenepropane-1,3-diol diacetate (99.8%) are introduced into the mixing chamber 4 through pipe 1, 2.400 kg per hour of methanol through pipe 2 and 0.008 kg per hour of sodium methylate (10% by weight in methanol) through pipe 3. The mixture flows through pipe 5 into the reaction column 6 which is operated under reflux and from which 2.580 kg per hour of an azeotropic mixture of methyl acetate and methanol boiling at 54° C are removed at the top through pipe 7. The sump product flows through pipe 8 into column 9 where methanol is withdrawn at the head through pipe 10 at the rate of 0.955 kg/hour. The sump is transferred through pipe 11 into the bottom of the hydrogenating column 13 which is filled with Raney nickel pellets, and into which hydrogen gas is forced under a pressure of 150 excess atmospheres in direct flow through pipe 12. The hydrogenation column is operated at a temperature of 75° C. The finished hydrogenation product enters the distillation apparatus 15 through pipe 14. From the distillation apparatus, the low-boiling constituents are removed through pipe 16 and the fused salt is removed through pipe 18, while 2-methylpropane-1,3-diol is removed through pipe 17 at the rate of 1.130 kg per hour, which corresponds to a yield of 90% of the theoretical quantity; boiling point 110° C/12 Torr, $n_D^{20}$ 1.4445. The hydrogenation catalyst used showed no signs of fatigue even after an operating time of 500 hours.

EXAMPLE 8

In a continuously operating plant corresponding to FIG. 1, 1.500 per hour of 2-methylenepropane-1,3-diol diacetate of the following composition are introduced into the mixing chamber 4 through pipe 1 (analytical values):
- 96.0% by weight of 2-methylenepropane-1,3-diol diacetate,
- 0.3% by weight of acetic acid,
- 0.4% by weight of water,
- 0.1% by weight of metallylacetate,
- 0.2% by weight of acetoxyacetone,
- 0.5% by weight of 2-methylenepropane-1,3-diol acetate,
- 1.3% by weight of unknown higher boiling substances, and 1.2% by weight of polymer. 2.560 kg of methanol per hour are introduced through pipe 2 and 0.026 kg of potassium hydroxide per hour (10% by weight in methanol) are introduced through pipe 3. The mixture then flows through pipe 5 into the reaction column 6 which is operated under reflux and from which 1.530 kg per hour of an azeotropic mixture of methyl acetate and methanol boiling at 54° C is removed at the head through pipe 7. The sump product flows through pipe 8 into column 9 where 1.650 kg per hour of methanol are removed at the head through pipe 10. The sump is passed through pipe 11 into the bottom of the hydrogenation column 13 which is filled with Raney nickel pellets, and hydrogen gas is forced in at a pressure of 150 excess atmospheres in the same direction of flow through pipe 12. The hydrogenation column is operated at a temperature of 80° C. The hydrogenated product passes through pipe 14 into the distillation apparatus 15, from which the low-boiling constituents are removed through pipe 16 and the fused salt through pipe 18, while 2-methylpropane-1,3-diol is removed through pipe 17 at the rate of 0.685 kg per hour, which corresponds to a yield of 91% of the theoretical quantity boiling point 110° C/12 Torr; $n_D^{20}$ 1.4444. The hydrogenation catalyst used showed no signs of fatigue even after an operating time of 500 hours.

EXAMPLE 9

In continuously operating plant corresponding to FIG. 2., 1.480 kg per hour of 2-methylenepropane-1,3-diol diacetate (99.8%) are introduced through pipe 1, 3.160 kg per hour of methanol through pipe 2 and 0.006 kg per hour of sodium methylate (10% by weight in methanol) through pipe 3. The components mixed in the mixing chamber 4 pass through pipe 5 into the reaction column 6 which is adjusted to the reflux temperature and from which 1.590 kg per hour of an azeotropic mixture of methyl acetate and methanol are removed at the head through pipe 7.

3.056 kg of the sump product are discharged from the foot of the column and fed into the bottom of the hydrogenation column 9 through pipe 8, while hydrogen is introduced into column 9 through pipe 10. The hydrogenation column is filled with a catalyst consisting of 1.0% by weight of ruthenium and 0.5% by weight of rhenium on lithium-aluminium spinel balls as carrier, and it is operated at a temperature of 62° C and under a hydrogen pressure of 30 excess atmospheres. The hydrogenated product passes through pipe 11 into a column 12 from which the low-boiling constituents, in particular methanol, are removed at the head through pipe 13, while the hydrogenation product itself is transferred through pipe 14 into the vacuum-operated distillation apparatus 15 from which 2-methylpropane-1,3-diol with a boiling point of 110° C/12 Torr, $n_D^{20}$ 1.4444, is distilled off through pipe 16 at the rate of 0.650 kg/hour (corresponding to 84% of the theoretical quantity) while the distillation residue is discharged through pipe 17.

EXAMPLE 10 (comparison example)

For comparison, an isolated and purified 2-methylene propane-1,3-diol is catalytically hydrogenated:

A mixture of 220 g of distilled 2-methylenepropane-1,3-diol (99.8%), 250 g of isopropanol and 20 g of Raney nickel is exhaustively hydrogenated at a hydrogen pressure of 50 excess atmosphere at 20° C. After working up the hydrogenation product by distillation, 157.1 g of 2-methyl-propane-1,3-diol, $n_D^{20}$ 1.4440, is obtained, which corresponds to 70% of the theoretical quantity.

When methanol is used instead of isopropanol, the yield is 153.4 g of 2-methylpropane-1,3-diol, $n_D^{20}$ 1.4446, which corresponds to 68% of the theoretical quantity.

What is claimed is:

1. A process for preparing 2-methylpropane-1,3-diol which comprises the steps of
    a. reacting 2-methylenepropane-1,3-diol diacetate at a temperature of 0° to 200° C with a monohydric $C_1$-$C_4$ aliphatic alcohol in excess of from 0.1 to 40 mols per mol of 2-methylenepropane-1,3-diol diacetate over the stoichiometric amount of said alcohol in the presence of a base selected from the group consisting of an alkali $C_1$-$C_4$ alcoholate, an alkali metal hydroxide, an alkali metal carbonate and a basic ion exchanger;
    b. adjusting thereafter the concentration of said alcohol, either by adding more alcohol or by distilling off excess alcohol, so that the reaction mixture contains from 0.1 to 30 mols of alcohol for each mol of 2-methylenepropane-1,3-diol diacetate initially reacted;
    c. and without isolating the resultant 2-methylenepropane-1,3-diol from step (a), thereafter catalytically hydrogenating it to form 2-methanepropane-1,3-diol employing a catalyst which hydrogenation component comprises Raney nickel, Raney nickel-iron, finely divided nickel on a carrier or a noble metal at a temperature of $-20°$ to 180° C.

2. A process according to claim 1 wherein the concentration of said alcohol is adjusted in step (b) so that the reaction mixture contains said alcohol in an amount of from 5 to 80% by weight, based on the weight of the reaction mixture.

3. A process according to claim 1 wherein the concentration of said alcohol is adjusted in step (b) after removing either all or part of the acetate of said alcohol formed during the reaction of step (a) by distillation.

4. Process of claim 1 wherein said $C_1$-$C_4$ aliphatic alcohol is a $C_1$-$C_4$ alkanol.

5. Process of claim 1 wherein the noble metal is platinum, ruthenium, rhodium or iridium.

6. Process of claim 1 wherein the base is an alkali metal alcoholate, alkali metal hydroxide, alkaline earth metal hydroxide or alkali metal carbonate.

7. Process of claim 1 wherein the reaction mixture contains from 0.14 to 10 mols of alcohol for each mol of 2-methylenepropane-1,3-diol diacetate initially reacted.

8. Process of claim wherein 1 the catalyst used for hydrogenation is Raney nickel or Raney nickel-iron.

9. Process of claim 1 wherein the catalyst used for hydrogenation is rhodium or ruthenium, optionally in combination with rhenium.

* * * * *